United States Patent
Graindorge

(10) Patent No.: US 7,020,515 B2
(45) Date of Patent: Mar. 28, 2006

(54) PRESENTATION OF DATA STORED IN AN ACTIVE IMPLANTABLE MEDICAL DEVICE TO ASSIST A PRACTITIONER'S DIAGNOSIS

(75) Inventor: Laurence Graindorge, Chatenay Malabry (FR)

(73) Assignee: ELA Medical S.A., Montrouge (FR)

( * ) Notice: Subject to any disclaimer, the term of this patent is extended or adjusted under 35 U.S.C. 154(b) by 561 days.

(21) Appl. No.: 10/115,489

(22) Filed: Mar. 27, 2002

(65) Prior Publication Data

US 2002/0169487 A1 Nov. 14, 2002

(30) Foreign Application Priority Data

Mar. 29, 2001 (FR) .................................. 01 04260

(51) Int. Cl.
*A61B 5/044* (2006.01)

(52) U.S. Cl. ........................................ 600/523; 607/32

(58) Field of Classification Search ................ 128/903, 128/920; 345/1.3, 4; 600/523; 607/30–32, 607/59–60

See application file for complete search history.

(56) References Cited

U.S. PATENT DOCUMENTS

| | | | |
|---|---|---|---|
| 5,487,755 A | 1/1996 | Snell et al. | 607/27 |
| 5,549,654 A | 8/1996 | Powell | 607/32 |
| 5,693,076 A * | 12/1997 | Kaemmerer | 607/59 |
| 5,697,959 A | 12/1997 | Poore | 607/32 |
| 5,724,985 A | 3/1998 | Snell et al. | 600/510 |
| 5,833,623 A * | 11/1998 | Mann et al. | 600/523 |
| 6,016,442 A | 1/2000 | Hsu et al. | 600/518 |

* cited by examiner

*Primary Examiner*—Robert E. Pezzuto
*Assistant Examiner*—Kristen Mullen
(74) *Attorney, Agent, or Firm*—Orrick Herrington & Sutcliffe LLP

(57) ABSTRACT

A process for the presentation of data stored in an active implantable medical device to assist a practitioner in making a diagnosis. This process includes the steps of: a) reading the raw implant data in the stored memory of the device, b) processing the raw data to elaborate a synthesis of the data, preferably through the use of an expert system, c) indexing the elaborated data synthesis according to a plurality of headings, each heading having associated therewith a set of specific implant data having contributed to the development of the heading, d) displaying on a screen (40), at the destination of a user, the aforementioned headings, in the form of a plurality of distinct display fields (41, 42, 43, 44) grouped on the same summary page (40), e) putting at the disposal of the user a tool for the individual selection of each one of the plurality of fields, and f) when a field of the summary page is selected at the choice of the user, displaying on the summary page (40) the aforementioned specific implant data (60) having contributed to the development of the heading corresponding to this selected field (41).

4 Claims, 5 Drawing Sheets

ATRIAL ARRHYTHMIAS

- There were four episodes of fallback.
- The marker chains confirm the presence of an atrial arrythmia.
- In the presence of atrial arrythmias, a

| START | | DURATION |
|---|---|---|
| S | 27/04 | 01:09 |
| R | 27/04 | 01:10 |
| S | 01/05 | 10:29 |
| S | 05/05 | 15:57 |
| R | 05/05 | 15:57 |

1h39

TIMING OF PP AND RR INTERVALS (MS)

- During the fallback, the ventricular rhythm is controlled by the stimulator.

FIG. 4

PRESENTATION OF DATA STORED IN AN ACTIVE IMPLANTABLE MEDICAL DEVICE TO ASSIST A PRACTITIONER'S DIAGNOSIS

FIELD OF THE INVENTION

The present invention is directed to "active implantable medical devices" as such devices are defined by the Jun. 20, 1990 directive 90/385/CEE of the Council of the European Communities, and more particularly to the pacemaker, defibrillator, cardiovertor and/or multisite devices for the treatment of the disorders of the heartbeat. The invention more precisely relates to the processing of data stored in read-write memory (RAM) of the device, such as histograms, curves, electrograms, etc.

BACKGROUND OF THE INVENTION

Data stored in an implant will be called hereafter "implant data". The implant data can be read by means of a programmer remote to the device using telemetry techniques that are in themselves well-known in the art.

The programmer typically cooperates with the implant to transmit the implant data from the device to a remote computer that will process the implant data and present the data in a form suitable for display on a screen, or for printing, e.g., a list of data and/or a graphic display. The processed data thus is presented to help the practitioner to analyze the history of the clinical data of the patient, and the operation of the pacemaker, over a period of several days or several weeks. The interpretation of such implant data will enable the practitioner to make a diagnosis.

Various techniques to assist the practitioner in making a diagnosis, allowing for an elaboration of the synthesis data starting from the raw implant data read from the implant, are known. One technique is, for example, the AIDA software ("Aide à l'Interpretation et au Diagnositc Automatiques" (Assistance to the Interpretation and to the Automatic Diagnosis)) available from ELA Medical, the assignee hereof. The functionalities of this AIDA software are described in the article by Limousin et al., "Value of Automatic Processing and Reliability of Stored Data in an inplanted Pacemaker: Initial Results in 59 Patients", *PACE;* 20[Pt.I]: 2893–2898 (1997). It will be noted that the present invention is not directed to the way in which the synthesis data are elaborated, which techniques are known to persons of ordinary skill in the art, nor to the diagnosis itself, which is made by the practitioner using the data synthesis elaborated by the software. The known techniques for performing the elaboration of the implant data into synthesis data are typically performed by expert systems (not forming apart of the present invention) such as a percentage or counts of events.

The elaborated synthesis data, in practice, are presented to the practitioner in the form of a series of screen pages, as illustrated, for example, on FIG. 1. A first series 10 of screens includes a display screen 11 having various statistics in a list as well as the evolution over time of the heart rate, i.e., a graphic chart of the raw implant data recorded in the implant. A screen 12 makes it possible to display a certain number of text messages and graphs to assist the diagnosis, i.e., elaborated synthesis data, for example, provided by a software program or functionality such as the software AIDA referred to above.

A second series 20 of screens illustrated in FIG. 1 makes it possible to display information relating to more particular aspects, for example, a screen 21 for the episodes of atrial tachycardia, a screen 22 for the atrio-ventricular intervals, and a screen 23 for the episodes of ventricular tachycardia.

Lastly, a third series 30 of screens provides more detailed information on particular aspects, such as the atrial context, the atrial intervals, the ventricular context or the ventricular intervals (respectively screens 31 to 34).

This organization of the displayed data is certainly very complete, since it makes it possible for the practitioner to reach a large amount of information and permits a fine (detailed) analysis, but it also presents the disadvantage of obliging the practitioner to consult multiple specialized and complex screens, requiring a lot of back-and-forth between different screens, all of which are complex.

This inconvenience is even greater for those practitioners that are not very familiar with the use of the software, in particular, those who must work with several different software programs (and there exist as many software program as pacemaker manufacturers), or the cardiologists, who are typically less specialized in the analysis of the implant data than the electrophysiologists, but who desire to be informed of certain recorded data to help them in a clinical diagnosis of the patient, to try, for example, to find certain revealing signs of a particular pathology.

OBJECTS AND SUMMARY OF THE INVENTION

One of the objects of the invention is, therefore, to propose a processing of implant data making it possible to organize and display the implant data in a more selective way, to facilitate the consultation of the implant data by the practitioner without making any concessions regarding the level of detail of the displayable data.

Broadly, the process is directed to gathering on the same summary display screen the most significant data in the form of a plurality of fields, and making it possible for the practitioner to choose and select a given field and see appear on this same screen (for example, in superposition) the specific data concerning the chosen field—and only that data concerning the chosen field.

More particularly, in a preferred embodiment, the process for the invention is a process for processing implant data, characterized by the stages (steps) including:

a) reading the raw implant data stored in the memory of the device;

b) elaborating the synthesis data starting from the raw stored implant data by means of an expert system;

c) indexing the data synthesis thus elaborated according to a plurality of headings with, associated with each heading, a set of specific implant data having contributed to the development of this heading, d) displaying on a screen, at the destination of a user, the aforementioned headings, in the form of a plurality of distinct display fields gathered on a common summary page, e) putting at the disposal of the user a means for individually selecting each one of the aforesaid fields, and f) when a field of the summary page is selected at the choice of the user, displaying on the summary page the aforementioned specific implant data having contributed to the development of the heading corresponding to the selected field.

The specific implant data can in particular include marker chains (i.e., a sequence or chain of event markers), cardiac frequency or amplitude (depolarization and/or stimulation)

histograms, electrograms, curves of cardiac events and/or time-stamped lists of events or graphically plotted data.

The display of the specific implant data at stage f) is advantageously a display of the specific implant data in superposition over the fields of the non selected headings.

The selection of stage e) can be a selection by a zone to be pointed or to be checked located inside the displayed field, or anywhere in the field.

BRIEF DESCRIPTION OF THE DRAWINGS

Other features, characteristics, and advantages of the present invention will appear to a person of ordinary skill in the art in view of the following detailed description of preferred embodiments of the present invention, made with reference to the annexed drawings, in which the same numerical and word references indicate similar elements, and in which:

FIG. 4 illustrates a summary screen in accordance with an alternate embodiment of the present invention, with display of the specific data relating to the selected one of the fields.

DETAILED DESCRIPTION OF THE INVENTION

Figure 2:
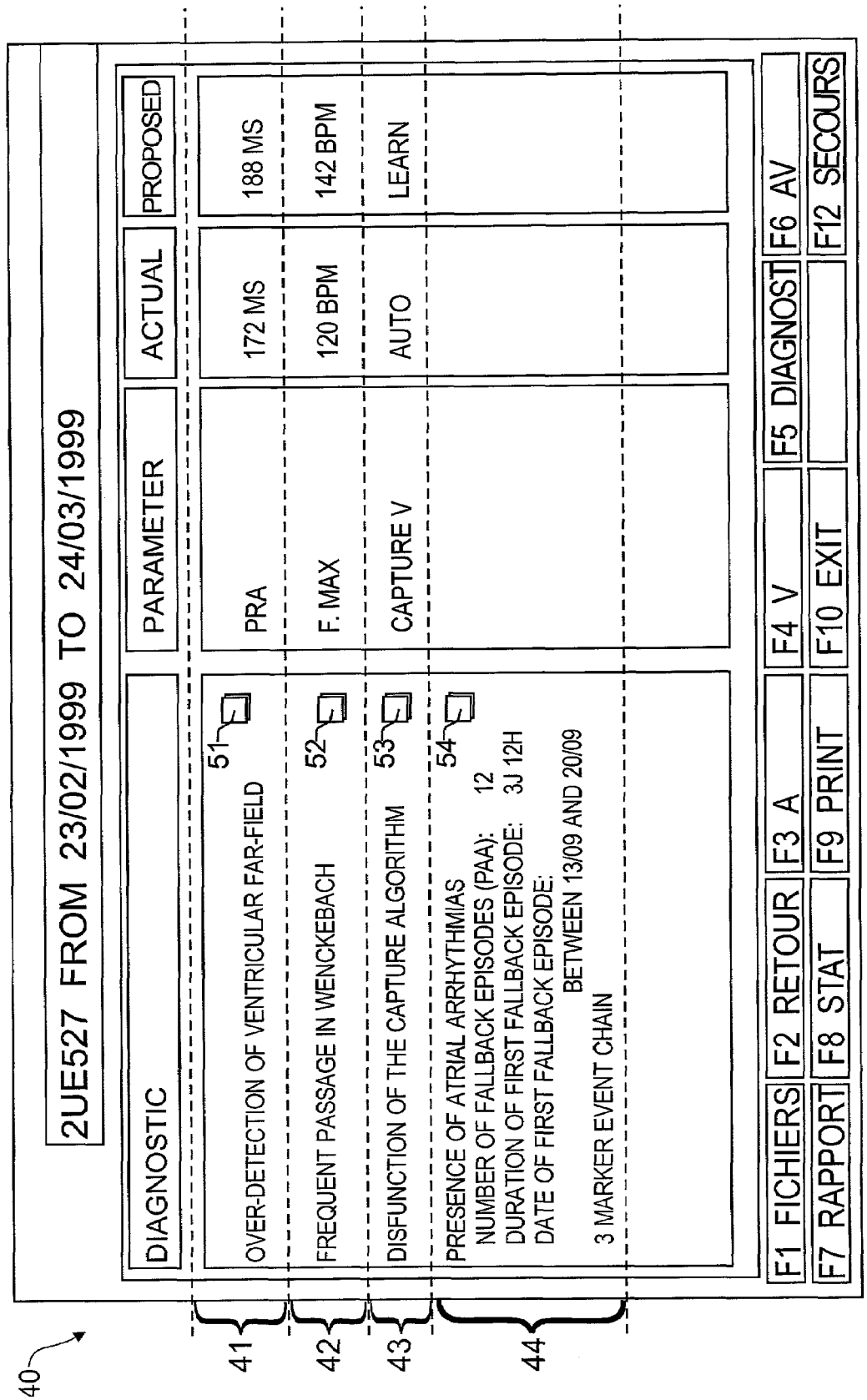
FIG. 2 illustrates a summary screen produced by the process of a first preferred embodiment of the present invention, before displaying specific data.

With reference to FIG. 2, a summary screen 40 produced by a preferred embodiment of the process of the invention is illustrated. This display screen 40 groups together elaborated data synthesis, for example, by a software such as the above mentioned software AIDA of ELA Medical. This software produces a certain number of messages to assist the practitioner in making a diagnosis, such as a first message "over-detection of ventricular far-field" (field 41), a second message "frequent passage in Wenckebach" (field 42), and a third message "dysfunction of the capture algorithm" (field 43), etc. More generally, the messages resulting from the analysis can include diagnoses on the existence of cardiac rate disorders, the programming of the apparatus, the effectiveness or the operation of the algorithms of the apparatus, etc. The text of these messages is displayed in distinct respective fields of display 41, 42, 43, 44 . . . , possibly also with short complementary indications, for example, the "parameter" concerned with the message, the actual current value of the parameter, and the proposed value suggested for a reprogramming of this parameter in order to cure the anomaly indicated by the message. It is noted that the development of the various indications of assistance to the diagnosis are in themselves known, and do not form part of the present invention, and the particular messages and fields are provided for illustration purposes.

Each field 41, 42 . . . comprises an individual means of selection by the practitioner, to the choice of this former, for example, by means of a respective boxes 51, 52, 53, 54, to which the practitioner will be able to point or check, e.g., placing on the box a cursor using a mouse, according to a well known technique of graphic use interface control. It also should be understood that selection of the field may be made by clicking, touching or pointing to any appropriate area in the field, and is not necessarily limited to a particular box appearing within the field; indeed, the entire field may be active such that a selection (mouseclick or the like) anywhere in the field can be effected by the practitioner.

It is also possible to envisage a selection by touching the screen or use of a light pen or voice recognition technique, or the like.

Figure 3:
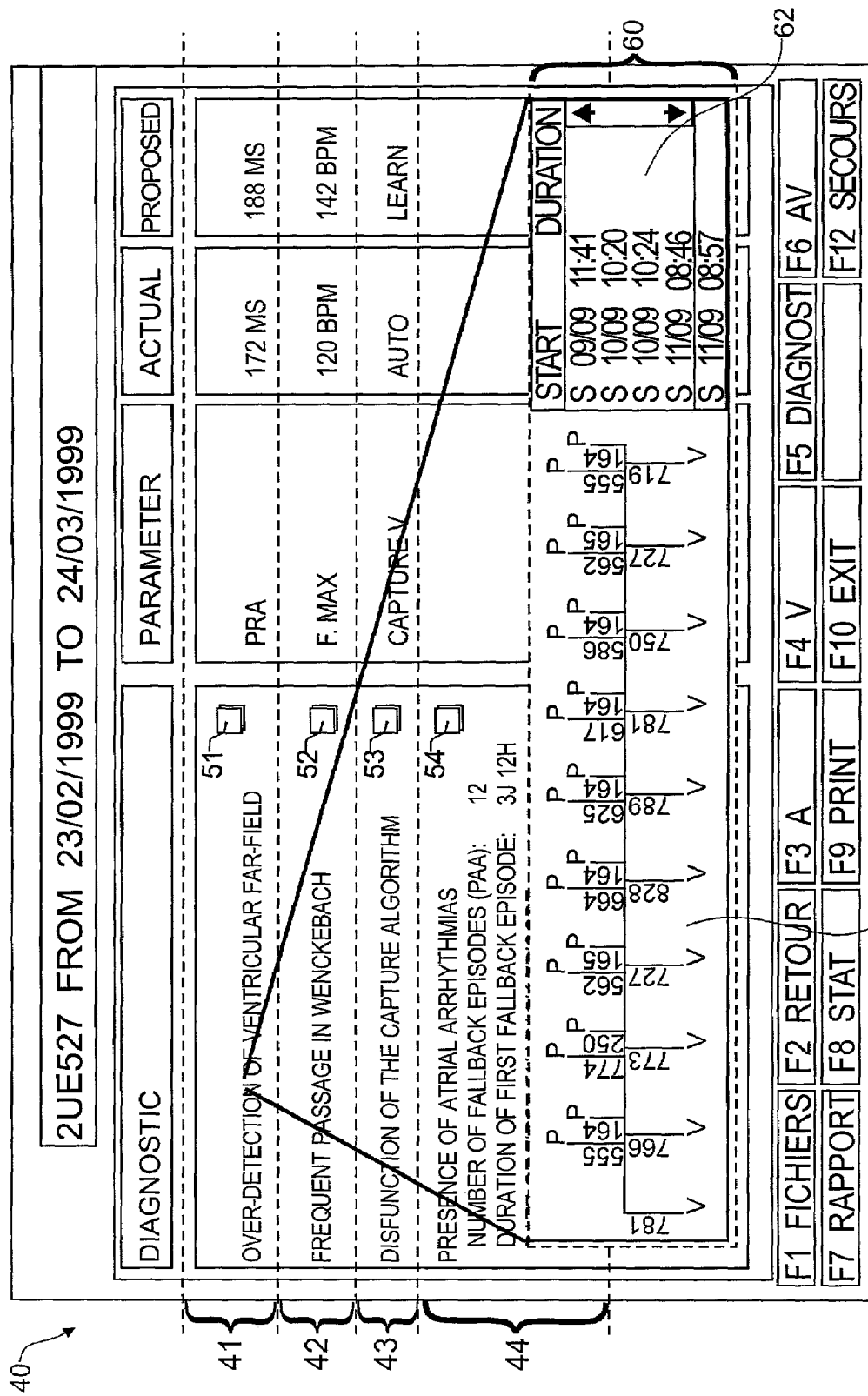
FIG. 3 illustrates the screen of FIG. 2, with a display of the specific data following the selection of a particular display field.

FIG. 3 illustrates the transformation of the display illustrated in FIG. 2 when the practitioner selects, for example, the field of display 41 by pointing on the associated box 51. This operation causes to reveal on the screen a block 60 comprising a certain number of specific data. Block 60, whose dimensions in the embodiment shown are smaller than those of page-screen 40, is preferably, displayed in superposition over the latter. Preferably, it is positioned to mask non-relevant information, i.e., information other than those of the selected display field 41, in the example described. The selection by the practitioner of one of the display fields, i.e., one of the presented messages that are of assistance to the diagnosis, will thus cause to be presented on the same screen at the same time the selected field, which remains visible, and a certain number of specific implant data grouped within a window of an appropriate size and preferably a smaller size than screen 40. The specific data presented in block 60 are the implant data which contributed to the development of the heading of the corresponding display field, e.g., field 41 in the illustrated example, where are showed the implant data whose analysis by the software produced a first message "Over-detection of ventricular far-field".

The practitioner can thus, simply by selecting the field corresponding to this first message "Over-detection of ventricular far-field", reveal the relevant implant data—and only that implant data—and thus refine the diagnosis by a finer analysis of these specific data.

Moreover, the visualization of the specific data or selection can make it possible for the practitioner to check the validity of the diagnoses proposed by the software.

Figure 1:
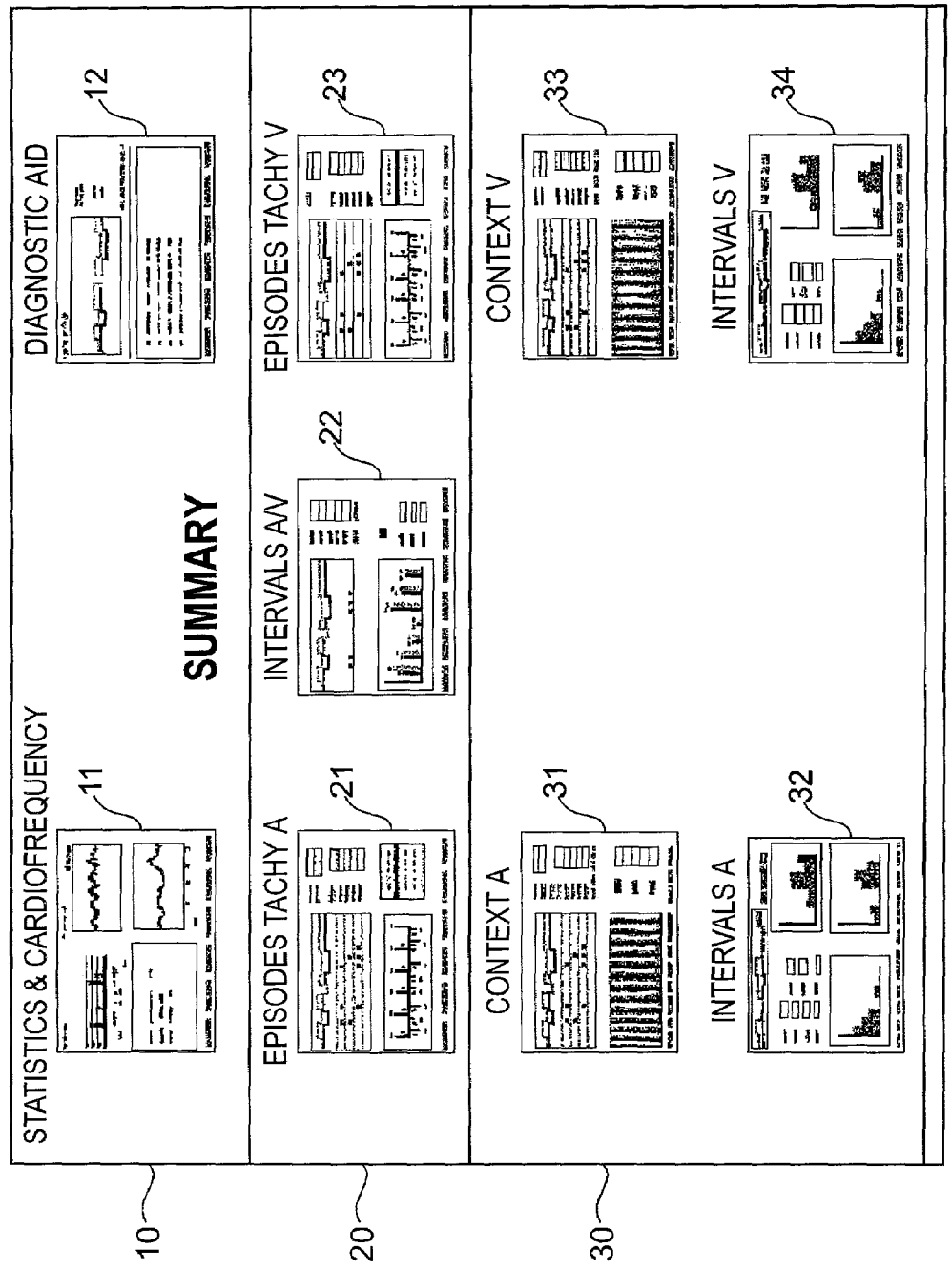
FIG. 1 illustrates the series of screens produced by the processes of the prior art.

It will be noted that the specific storage block is displayed without commutation of pagescreen 40, unlike the prior art technique where, as illustrated in FIG. 1, it was necessary for the practitioner to navigate through a tree structure of different page-screens to find the relevant data, and even then the relevant data could be dispersed over different several screens.

In addition, insofar as the messages respectively displayed in various fields 41, 42 . . . on a summary-page 40 correspond to symptoms which are often dependent between them, it can be interesting for the practitioner to quickly pass from one specific data block to the other, which can be done very quickly and easily simply by pointing/clicking on the corresponding box 51, 52 . . . , with the summary screen 40 always remaining displayed in the background. Thus, the present invention is unlike the prior art system which proceeded according to a substitution of screens, and not by a selective superposition of relevant information.

The specific data displayed in block 60 can have various forms. On FIG. 3, one thus illustrates a chain of event markers 61 presented in the form of a chronogram, and a time-stamped series of events presented in the form of a rolling (scrolling) list 62. Other types of specific data can of course be displayed, in various forms: curves, histograms, etc. In addition, the nature and the presentation of the specific data may vary according to the selected display field, because displayed in the block the 60 are only the specific data having contributed to the development of the corresponding heading of the selected field.

Figure 5:
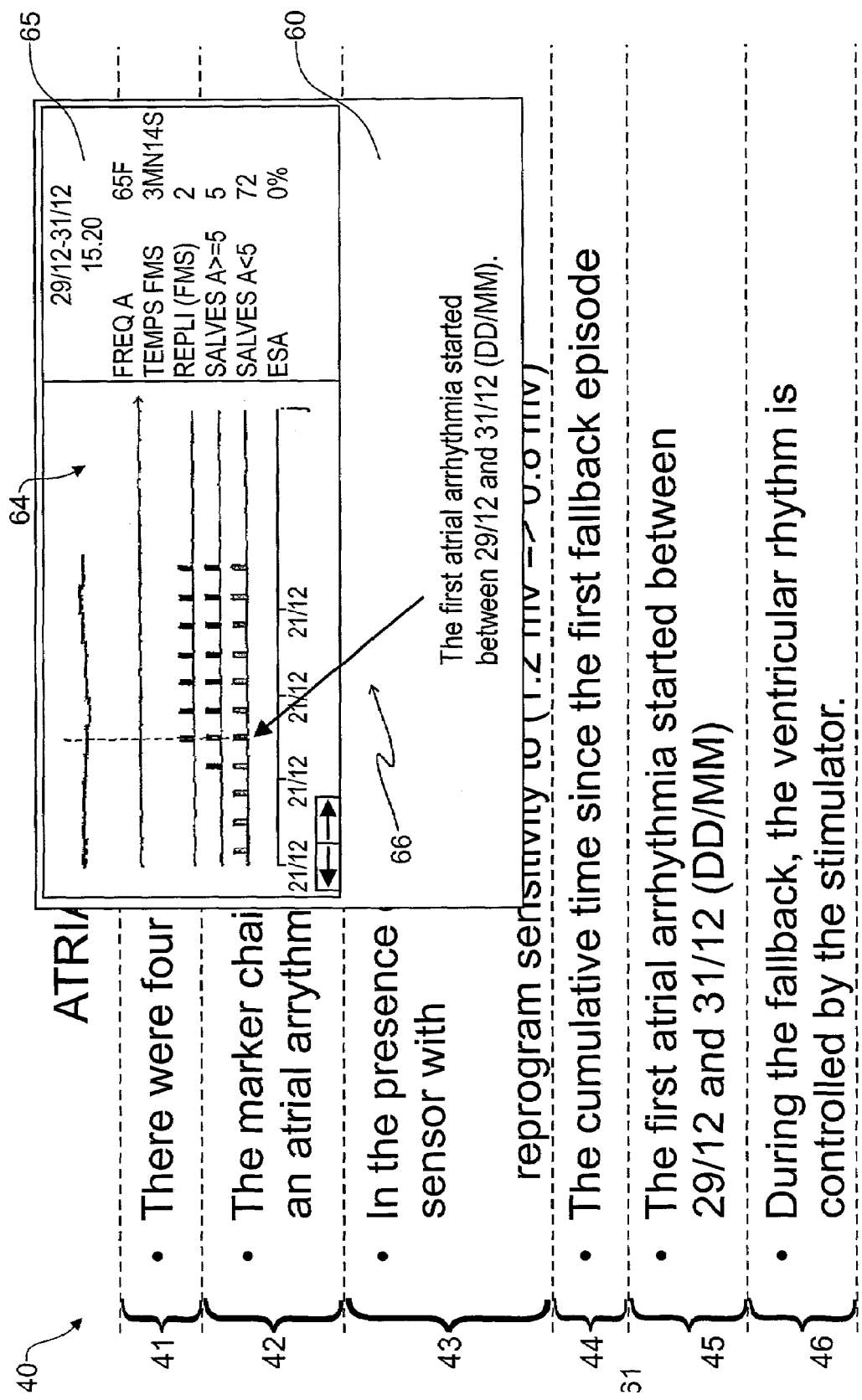
FIG. 5 is homologous with FIG. 4 but for the display of the specific data relating to another selected field.

FIGS. 4 and 5 illustrate another preferred embodiment of the process according to the present invention. In this embodiment, the summary page screen 40 is presented simply in the form of a series of literal messages appearing in corresponding fields.

For example, in the case of an atrial arrhythmia, the summary page 40 displays the following: a first message "There were 4 episodes of fall-back" (Field 41), a second message "the markers chains confirm the presence of an atrial arrhythmia" (Field 42), etc.

Each one of these messages corresponds to a field 41, 42 . . . 46 on the screen. The practitioner can select one of these fields, for example, by placing the cursor in an a specified (or unspecified) place within the field, or by means of a displacement key of a keyboard, by voice command, touch screen, etc.

The selection of a field starts the appearance of a specific storage block 60, in superposition on the other fields of the screen, to leave apparent the message of the selected field. Thus, on FIG. 4, selection of field 42 makes appear a window 60 partially masking fields 43, 44 and 45, while on FIG. 5 selection of field 45 makes appearing a window 60 masking fields 41, 42 and 43.

In the case of FIG. 4, the selection of field 42 corresponds to the second message of assistance to the diagnosis "the chains of markers confirm the presence of atrial arrlythmias" and produces the display of a specific data block 60 including a chronogram 61 of the marker chain, the time-stamped list 62 of the arrhythmias that were detected, with their moment of appearance and their duration, as well as a graph 63 showing the evolution of the cardiac intervals. Alternately, a time-stamped list of sensor data events also could be produced as a display.

On FIG. 5, the selection of field 45 corresponding to the fifth message of assistance to the diagnosis "the first atrial arrhythmia started between the 29/12 and the 31/12" produce the display of a block 60 including a series of chronograms 64 reflecting the evolution of the atrial rate, a table 65 presenting the statistical results of a number of parameters over the studied period (e.g. in this example Atrial Frequency, duration, fallback episodes, Salvos>S, Salvos<S and Atrial Extrasystoles (AES)), as well as an arrow 66 pointing to the chronogram at the moment of which has occurred of the first arrhythmia indicated in the fifth message of field 45. A "salvo" is a paroxystic atrial tachycardia, and the "S" is a corresponding threshold. Also, the fifth message of field 45 optionally can be displayed within block 60, as illustrated. Thus, it is possible that the superposition can mask the selected field. It also is preferred that the window 60 can be hidden or closed by a mouse click or keystroke (e.g., the "esc" key) so as to bring the full page screen 40 into view, so as to facilitate selection of another field without changing screen 40. Software suitable for presenting the active fields and opening and closing of the data fields is believed to be within the programming abilities of a person of ordinary level of skill in the art using a conventional window style operating system (Windows, OS, Linux, etc.).

One skilled in the art will appreciate that the present invention can be practiced by other than the described embodiments, which are presented for purposes of illustration and not of limitation.

I claim:

1. A process for processing raw implant data stored in the memory of an active implantable medical device, in particular of a pacemaker, a defibrillator, a cardiovertor and/or a multisite device, comprising:
   a) reading the raw implant data stored in the memory of the device;
   b) processing the raw data to elaborate a data synthesis by means of an expert system;
   c) generating and indexing from the elaborated data synthesis a plurality of headings, each heading having associated therewith a set of specific implant data having contributed to the development of said heading;
   d) displaying on a screen a plurality of headings in a corresponding plurality of distinct display fields grouped on a summary page;
   e) selecting one of said plurality of fields; and
   f) displaying, in response to a selected field, said specific implant data having contributed to the development of the heading corresponding to said selected field.

2. The process of claim 1, wherein displaying the specific implant data further comprises displaying at least one of a chain of markers, a cardiac frequency histogram, a cardiac depolarization/stimulation amplitude histogram, a curve of stored cardiac events, a time-stamped list of cardiac events, and a time-stamped list of sensor data events.

3. The process of claim 1, wherein displaying the specific implant data further comprises displaying said implant data in superposition on the fields of the non-selected headings.

4. The process of claim 1, wherein step e) further comprises providing each said field with a zone inside the field to be activated to effect the selection.

* * * * *